United States Patent
Brooks et al.

(10) Patent No.: US 8,290,577 B2
(45) Date of Patent: Oct. 16, 2012

(54) METHODS AND APPARATUS FOR ENHANCED FIDUCIAL POINT DETERMINATION AND NON-INVASIVE HEMODYNAMIC PARAMETER DETERMINATION

(76) Inventors: Donald J. Brooks, San Diego, CA (US); Jeremy Malecha, San Diego, CA (US)

( * ) Notice: Subject to any disclaimer, the term of this patent is extended or adjusted under 35 U.S.C. 154(b) by 1275 days.

(21) Appl. No.: 11/894,989

(22) Filed: Aug. 21, 2007

(65) Prior Publication Data
US 2008/0234594 A1    Sep. 25, 2008

Related U.S. Application Data

(60) Provisional application No. 60/919,725, filed on Mar. 23, 2007.

(51) Int. Cl.
*A61B 5/04* (2006.01)
(52) U.S. Cl. .......................... 600/513; 600/528
(58) Field of Classification Search .................. 600/513, 600/510, 484, 509, 506, 526, 393, 521, 528
See application file for complete search history.

(56) References Cited

U.S. PATENT DOCUMENTS

| 4,548,204 | A |   | 10/1985 | Groch |         |
|-----------|---|---|---------|-------|---------|
| 5,178,154 | A | * | 1/1993  | Ackmann et al. | 600/526 |
| 5,748,758 | A | * | 5/1998  | Menasco et al. | 381/176 |
| D471,281  | S |   | 3/2003  | Baura |         |
| D475,138  | S |   | 5/2003  | Baura |         |
| 6,561,986 | B2| * | 5/2003  | Baura et al. | 600/526 |
| 6,602,201 | B1|   | 8/2003  | Hepp et al. |    |
| 6,636,754 | B1|   | 10/2003 | Baura |         |
| 6,947,789 | B2|   | 9/2005  | Selvester et al. |   |
| 7,043,293 | B1|   | 5/2006  | Baura |         |
| 7,096,060 | B2|   | 8/2006  | Arand et al. |   |
| 7,139,609 | B1|   | 11/2006 | Min et al. |     |
| 7,146,206 | B2|   | 12/2006 | Glass et al. |   |
| 7,149,576 | B1|   | 12/2006 | Baura et al. |   |
| 7,214,107 | B2|   | 5/2007  | Powell et al. |  |
| 2002/0151938 | A1 |   | 10/2002 | Corbucci |    |
| 2003/0060723 | A1 | * | 3/2003  | Joo et al. | 600/510 |
| 2004/0167416 | A1 | * | 8/2004  | Lee | 600/513 |
| 2004/0167417 | A1 |   | 8/2004  | Schulhauser et al. | |
| 2004/0243192 | A1 |   | 12/2004 | Hepp |        |
| 2004/0254481 | A1 |   | 12/2004 | Brodnich |    |
| 2005/0124901 | A1 | * | 6/2005  | Misczynski et al. | 600/509 |
| 2006/0100535 | A1 |   | 5/2006  | Bauer |       |
| 2006/0111642 | A1 |   | 5/2006  | Baura |       |
| 2007/0049977 | A1 | * | 3/2007  | Von Arx et al. | 607/9 |
| 2007/0213625 | A1 |   | 9/2007  | Nayak |       |

* cited by examiner

*Primary Examiner* — Eric D. Bertram
*Assistant Examiner* — Roland Dinga

(57) ABSTRACT

Methods and apparatus for utilizing multiple sources of physiologic data to enhance measurement robustness and accuracy. In one embodiment, phonocardiography or "heart sounds" data is used in combination with one or more other techniques (for example, impedance cardiography or ICG waveforms, and/or electrocardiography or ECG waveforms) to provide more accurate and robust physiological and/or hemodynamic assessment of living subjects. In one variant, the aforementioned methods and apparatus are used to improve ICG fiducial point (e.g., B, C and X point) detection and identification accuracy. Moreover, the new ICG fiducial points that may be clinically important may be identified using the disclosed methods and apparatus. In a further aspect, the invention discloses methods and apparatus for utilization of ICG and/or ECG waveform information to improve the identification and characterization of heart sounds (such as e.g., S1, S2, S3, or S4 heart sounds), murmurs, and other such artifacts or phenomena.

35 Claims, 7 Drawing Sheets

METHODS AND APPARATUS FOR ENHANCED FIDUCIAL POINT DETERMINATION AND NON-INVASIVE HEMODYNAMIC PARAMETER DETERMINATION

PRIORITY

The present application claims priority benefit of U.S. provisional patent application Ser. No. 60/919,725 filed Mar. 23, 2007 of the same title, which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

1. Field of the Invention

This invention relates generally to the field of physiologic analysis of living subjects, and particularly in one exemplary aspect to an apparatus and methods for non-invasively detecting and evaluating the cardiac or hemodynamic function of a subject using, inter alia, heart sounds.

2. Description of Related Technology

In the field of assessing cardiac or hemodynamic function in a living subject, a multitude of techniques currently exist. One such technology for assessing cardiac function is the well known electrocardiogram or ECG. An ECG is an output produced by an electrocardiograph which illustrates (e.g., graphically) the electrical activity of the subject's heart over time. By utilizing ECG techniques, diagnostic information about the cardiac function of a living subject can be obtained. Among other applications, ECG has become particularly well known for its use in detecting cardiac arrhythmias.

On such example of the use of ECG technology is disclosed in U.S. Pat. No. 6,947,789 to Selvester, et al. issued Sep. 20, 2005 and entitled "Method for detecting, sizing and locating old myocardial infarct" which discloses algorithms for detecting, sizing and locating old myocardial infarcts by evaluating ECG lead data derived from selected ECG leads. For a given human subject, the specific hierarchical pattern of lead data to be examined is selected on the basis of predetermined personal and demographic data.

So called impedance cardiography (ICG), also referred to as thoracic electrical bio-impedance (TEB) and electrical impedance plethysmography (EIP) is another common prior art method for assessing cardiac or hemodynamic function in a living subject. ICG utilizes the placement of sensors (typically on the neck and chest or thorax of the subject) which are then used to transmit and detect electrical and impedance changes in the thorax of a living subject. These electrical and impedance changes are then used to measure and calculate various hemodynamic parameters of the living subject. Exemplary ICG devices and techniques are described in, inter alia, U.S. Pat. No. 6,561,986 to Baura, et al. issued May 13, 2003 entitled "Method and apparatus for hemodynamic assessment including fiducial point detection" U.S. Pat. No. 6,602,201 to Hepp, et al. issued Aug. 5, 2003 and entitled "Apparatus and method for determining cardiac output in a living subject", U.S. Pat. No. 7,043,293 to Baura issued May 9, 2006 entitled "Method and apparatus for waveform assessment", and U.S. Pat. No. 7,149,576 to Baura, et al. issued Dec. 12, 2006 entitled "Apparatus and method for defibrillation of a living subject", each of the foregoing being incorporated herein by reference in its entirety.

The recording of heart sounds (i.e. the sounds generated by the beating heart and/or the resultant flow of blood) is another technique utilized to ascertain cardiac and/or hemodynamic function of a living subject. In the well known technique of cardiac auscultation, a caregiver uses a stethoscope to listen for these sounds, which can also provide important clues into the condition of the heart. There are four major functional areas of auscultation of the heart (i.e., aortic, pulmonic, tricuspid, and mitral. They are named for the valve that they best assess.

Normal human heart sounds are produced by, inter alia, closure of the valves of the heart muscle. Flow through these valves will affect the sound made. Thus, in situations of increased blood flow (e.g., strenuous exercise), the intensity of the heart sounds may be increased. In situations of lower blood flow (e.g., shock), the intensity of the heart sounds may be decreased.

Normal heart sounds include so-called S1 and S2 sounds. The S1 sound is normally the first heart sound heard (best heard in the mitral area), and corresponds to closure of the mitral and tricuspid (AV) valves, as well as the opening of the aortic valve. A normal S1 sound is typically lower-pitched, and of longer duration than, S2.

The S2 sound is normally the second sound heard (best heard over the aortic area), and corresponds to closure of the pulmonic and aortic valves. A normal S2 is higher-pitched and of shorter duration than S1. S2 is also normally louder (greater amplitude) than S1.

Abnormal human heart sounds comprise the S3 and S4 sounds. The S3 sound is heard immediately following S2, and may be considered normal in children and adolescents, but usually disappears in adults. When heard in adults, an S3 may indicate left ventricular failure.

The S4 sound is heard immediately before the S1. It may be present in infants and children. The S4 is produced by a decreased compliance of the ventricle, and may indicate myocardial infarction (i.e., heart attack) or shock.

Many factors can affect heart sounds in a human, and may produce alterations in both the normal and abnormal sounds. These include for example congenital defects, previous cardiac disease, and patient age.

Moreover, heart murmurs may be generated by a turbulent flow of blood, and may occur inside or outside the heart. Abnormal murmurs can be caused by, inter alia, stenosis or a restriction of the opening of a heart valve, causing turbulence as blood flows through it. Valve insufficiency (or regurgitation) allows backflow of blood when the incompetent valve is supposed to be closed. Different murmurs are audible in different parts of the cardiac cycle, depending on the cause of the murmur.

More recently, techniques have been proposed which combine differing cardiac assessment techniques (such as ECG and heart sounds) in order to improve the assessment of cardiac function in a living subject. For example, U.S. Pat. No. 4,548,204 to Groch, et al. issued Oct. 22, 1985 and entitled "Apparatus for monitoring cardiac activity via ECG and heart sound signals" discloses a technique where from a heart sound signal input the occurrence of a first occurring heart sound is detected. Thereupon a predetermined heart sound enable window time is established, which for a first detection cycle is set to approximately the diastolic interval for the maximum heart rate to be detected. If a second heart sound occurs within this heart sound enable window time, this second heart sound is detected as a systole heart sound.

The first heart sound may be detected as a diastole heart sound. If a second heart sound does not occur within the heart sound enable window time the procedure is repeated with increasing heart sound enable time as long as a second heart sound occurs within an increased heart sound enable window time. For monitoring remotely or by a using recording, an ECG signal is modulated and combined with the associated heart sound signal for use as a single combined signal.

U.S. Pat. No. 7,096,060 to Arand, et al. issued Aug. 22, 2006 and entitled "Method and system for detection of heart sounds" discloses a method and system for automatically detecting heart sounds. The sound system receives sound data corresponding to beats of the heart. The sound system analyzes the sound data to detect the presence of a heart sound within the beats. The sound system then outputs an indication of the heart sounds that were detected. The sound system may use ECG data to identify various locations (e.g., R peak) within a beat and use those locations to assist in the detection of heart sounds.

U.S. Pat. No. 7,139,609 to Min, et al. issued Nov. 21, 2006 and entitled "System and method for monitoring cardiac function via cardiac sounds using an implantable cardiac stimulation device" discloses techniques for performing internal measurement of heart sounds to estimate patient cardiac function in terms of stroke volume, cardiac output, or a maximum rate of change of aortic pressure with time (max dP/dt). Control parameters of the medical device are then automatically adjusted so as to optimize overall cardiac function or to provide for ventricular resynchronization therapy. In one example, heart sound signals are derived from acceleration signals received from an accelerometer. The heart sound signals are analyzed to identify S1 and S2 heart sounds as well as ejection period and isovolumic interval (ISOV). Proxies for max dP/dt, stroke volume and cardiac output are then derived from the S1 and S2 heart sounds, the ejection period and the ISOV. Alternative techniques, not requiring detection of ISOV, are also disclosed and employed for use if the patient has heart value regurgitation.

United States Patent Publication No. 20020151938 to Corbucci, published on Oct. 17, 2002 and entitled "Myocardial performance assessment" discloses a technique whereby myocardial performance is assessed using a combination of electrical and mechanical criteria. More specifically, this assessment may be based on a QT interval based on electrogram (EGM) readings and on first and second heart sounds. The timing relationships between the QT interval and the first and second heart sounds can be used to evaluate certain systolic, diastolic, and systolic/diastolic parameters relating to myocardial performance. In addition, these parameters may be used to drive therapies. For example, myocardial performance parameters obtained from the QT interval and from the timing of the first and second heart sounds may be used to optimize the AV delay and to optimize multi-site pacing.

United States Patent Publication No. 20040167417 to Schulhauser, et al. published Aug. 26, 2004 and entitled "Apparatus and method for chronically monitoring heart sounds for deriving estimated blood pressure" discloses a minimally invasive, implantable heart sound and ECG monitor and associated methods for deriving blood pressure from heart sound data. The device is equipped with an acoustical sensor for detecting first and second heart sounds which are sampled and stored during sensing windows following R-wave and T-wave detections, respectively. ECG and heart sound data are stored in a continuous, looping memory, and segments of data are stored in long-term memory upon an automatic or manual data storage triggering event. Estimated blood pressure is calculated based on custom spectral analysis and processing of the first and second heart sounds. A calibration method includes measuring a patient's blood pressure using a standard clinical method and performing regression analysis on multiple spectral variables to identify a set of best fit weighted equations for predicting blood pressure. Concurrent ECG and estimated blood pressure may be displayed for review by a physician.

United States Patent Publication No. 20040254481 to Brodnick, published Dec. 16, 2004 and entitled "Methods and systems for monitoring respiration" discloses a method for determining respiration rate in a patient that can include various parts. The respiration rate can be determined by measuring the heart's S2 split. The S2 split can be identified by observing the timing of the heart sounds. Other respiration related information, such as respiration phase and the occurrence of apnea, can be identified as well. A respiration monitor of this type may be useful for monitoring sub-acute patients, and outpatients. A sensor for the respiration monitor and an electrode for an ECG monitor may be combined into a single probe.

United States Patent Publication No. 20060100535 to Bauer published May 11, 2006 and entitled "Integrated, plural-signal, heart-signal sensor system and related data-presentation methodology" discloses a system and a related methodology for gathering, during a selected time span, and from a common anatomical site, time-contemporaneous ECG-electrical and heart-sound signals including (1) processing such signals to effect (a) time-based, related ECG fiducials, and (b) systolic and diastolic heart-sound indicators, and (2) creating a reportable data stream which communicates such effected fiducials and indicators in a manner whereby time-based relationships between them, and non-time-based differentiation between systolic and diastolic heart-sound indicators, are made visually discernible. The methodology of the invention may also be implemented strictly for the gathering and processing of heart sounds.

Despite the foregoing variety of techniques, there remains a salient need for improved apparatus and methods for the assessment of cardiac and/or hemodynamic function in a living subject, including especially the diagnosis of particular cardiac and hemodynamic conditions and phenomena within the subject being evaluated. Ideally, such improved apparatus and methods would make use of technologies generally familiar to practitioners while offering additional tools and techniques which provide, for example, confirmatory analysis of observed cardiac/hemodynamic function. Such improved apparatus and methods would also add to and utilize the strengths of existing techniques, while simultaneously minimizing the drawbacks of those same techniques through the combination of differing but complementary analyses.

SUMMARY OF THE INVENTION

The present invention satisfies the foregoing needs by providing, inter alia, improved apparatus and methods for cardiac function assessment.

In a first aspect of the invention, a method of assessing cardiac function within a living subject is disclosed. In one embodiment, the method comprises: obtaining: (i) acoustic information relating to the cardiac system of said subject; (ii) electrocardiographic information relating to said subject; and (iii) impedance cardiographic information relating to said subject; and utilizing said acoustic, electrocardiographic and impedance information substantially in concert to assess cardiac function.

In a second aspect of the invention, a method of evaluating or detecting one or more acoustic artifacts or features within a waveform is disclosed. In one embodiment, the method comprises using a known fiducial point in a first waveform (e.g., R point within ECG) to identify or validate one or more heart sounds (e.g., S1 or S2).

In a third aspect of the invention, an improved method of determining at least one hemodynamic parameter or function associated with a living subject is disclosed. In one exemplary embodiment, the hemodynamic parameter comprises cardiac output, and the method comprises utilizing heart sounds in conjunction with ICG and ECG signals to provide a cardiac output measurement of improved accuracy and robustness.

In a fourth aspect of the invention, a method of detecting specific events or artifacts within a hemodynamic parametric waveform is disclosed. In one exemplary embodiment, the waveform comprises a heart sounds acoustic waveform, and the method comprises using an R point of an ECG to more accurately detect the S1 and S2 events (as well as detection of specific areas or features of the S1 and S2 sounds). In another embodiment, the waveform comprises an ICG waveform, and the method comprises using the S1 and S2 events to more accurately detect artifacts of interest (e.g., aortic valve operation). By more accurately detecting these hemodynamic parameters and events, results of therapy can be monitored, trends can be better tracked, and other such evaluations conducted that would not be feasible with less accurate measurements.

In a fifth aspect of the invention, an improved computer program for implementing the aforementioned methods is disclosed. In a first exemplary embodiment, the computer program comprises an object code representation of an assembly language source code listing, the object code representation being disposed on a transportable storage medium (e.g., floppy disk). In a second embodiment, the computer program is disposed on the discrete storage device of a signal processing apparatus and adapted to run on the digital processor thereof. The computer program further comprises a graphical user interface (GUI) operatively coupled to the display and input device of the signal processing apparatus. One or more subroutines or algorithms for implementing the methodologies above are included within the program. In a third exemplary embodiment, the computer program comprises an instruction set disposed within the storage device (such as the embedded program memory) of the digital signal processor (DSP) of the signal processing apparatus.

In a sixth aspect of the invention, an improved apparatus for assessing one or more hemodynamic parameters associated with a living subject is disclosed. In one exemplary embodiment, the hemodynamic parameter under evaluation comprises the cardiac output of the subject, and the apparatus generally comprises a plurality of electrodes disposed in proximity to the thoracic cavity of the subject; a current source adapted to provide a predetermined current through the thoracic cavity of the subject via at least one of the plurality of electrodes; and a signal processing apparatus adapted to analyze the signals obtained from the electrodes and determine stroke volume (and accordingly cardiac output) therefrom. The signal processing apparatus comprises a signal conditioning apparatus adapted to process signals (including the impedance signal(s), heart sounds and ECG derived from one or more of the electrodes) and produce conditioned signals relating thereto; and a processor adapted to detect the fiducial points within the impedance signal(s) or conditioned signals, from which cardiac output is ultimately determined.

In a seventh aspect of the invention, an improved method of providing treatment to a subject using the aforementioned methodology is disclosed.

In an eighth aspect, an improved physiologic sensor is disclosed. In one embodiment, the sensor comprises a disposable sensor that integrates heart sounds, ICG and ECG signal capability into one apparatus.

In a ninth aspect of the invention, methods and apparatus for increasing the clinical robustness of a physiologic determination system are disclosed. In one embodiment, the system comprises an ICG system, and the methods/apparatus utilize one or more heart sounds to aid in validation and/or detection of artifacts or features in the ICG waveform.

In a tenth aspect of the invention, improved defibrillation apparatus and methods using heart sound, ICG and ECG data are disclosed.

In an eleventh aspect of the invention, methods and apparatus for the identification of one or more physiologic conditions using heart sounds information coupled with ICG and/or ECG data is disclosed.

DETAILED DESCRIPTION OF THE INVENTION

Figure 1:
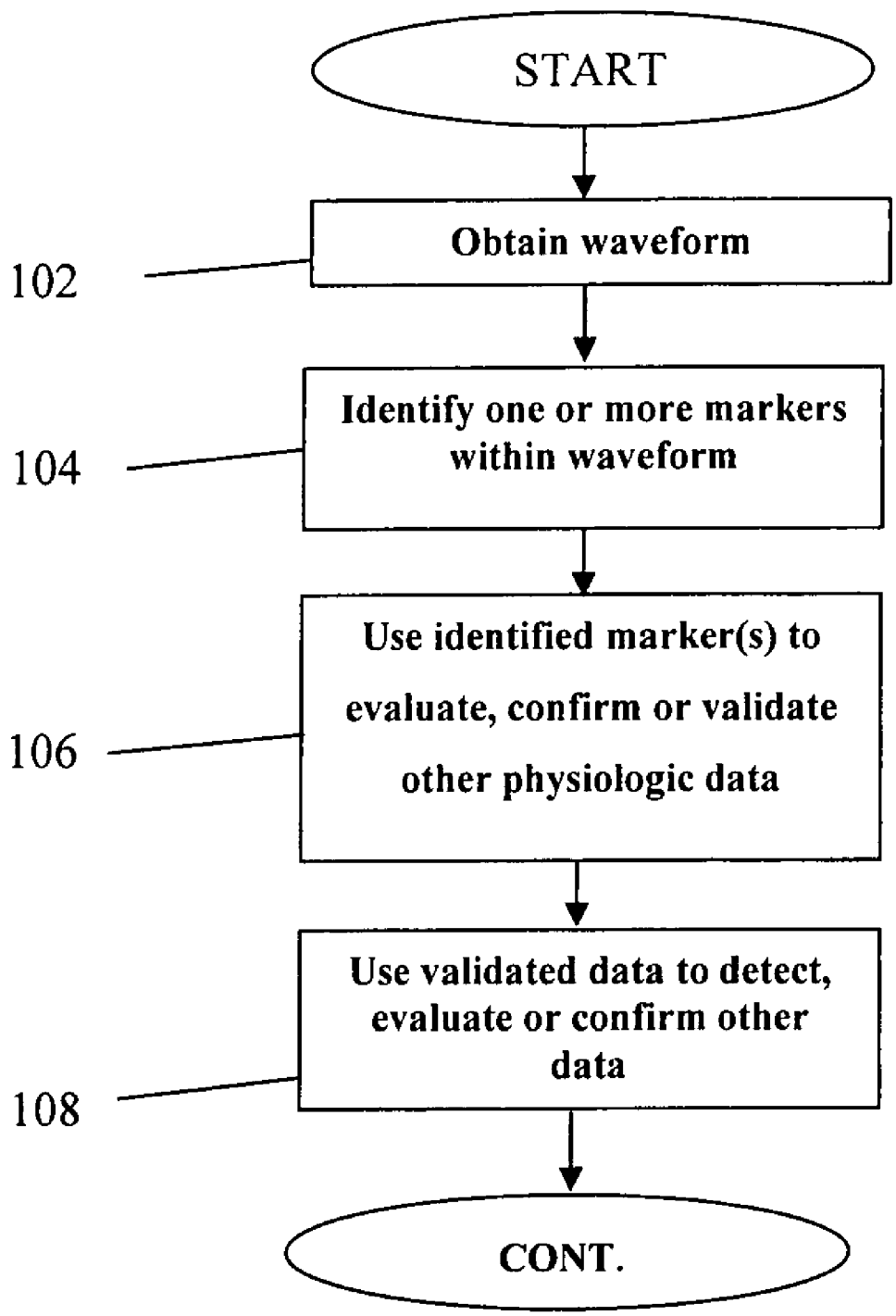
FIG. 1 is a logical flow diagram illustrating one embodiment of the generalized method of using multiple sources of physiologic information to increase the robustness of a physiologic measurement or determination.

Reference is now made to the drawings wherein like numerals refer to like parts throughout.

As used herein, the term "software application" refers generally to a unit of executable software that implements a certain functionality or theme. The themes of applications vary broadly across any number of disciplines and functions (such as on-demand content management, e-commerce transactions, brokerage transactions, home entertainment, calculator etc.), and one application may have more than one theme. The unit of executable software generally runs in a predetermined environment; for example, the unit could comprise a downloadable Java Xlet™ that runs within the JavaTV™ environment.

As used herein, the term "computer program" or "software" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VOXML), and the like, as well as object-oriented environments such as the Common Object Request Broker Architecture (CORBA), Java™ (including J2ME, Java Beans, etc.), Binary Runtime Environment (e.g., BREW), and the like.

As used herein, the term "display" means any type of device adapted to display information, including without limitation CRTs, LCDs, TFTs, plasma displays, LEDs, incandescent and fluorescent devices. Display devices may also include less dynamic devices such as, for example, printers, e-ink devices, and the like.

As used herein, the term "integrated circuit (IC)" refers to any type of device having any level of integration (including without limitation ULSI, VLSI, and LSI) and irrespective of process or base materials (including, without limitation Si, SiGe, CMOS and GaAs). ICs may include, for example, memory devices (e.g., DRAM, SRAM, DDRAM, EEPROM/Flash, ROM), digital processors, SoC devices, FPGAs, ASICs, ADCs, DACs, transceivers, memory controllers, and other devices, as well as any combinations thereof.

As used herein, the terms "Internet" and "internet" are used interchangeably to refer to inter-networks including, without limitation, the Internet.

As used herein, the term "memory" includes any type of integrated circuit or other storage device adapted for storing digital data including, without limitation, ROM. PROM, EEPROM, DRAM, SDRAM, DDR/2 SDRAM, EDO/FPMS, RLDRAM, SRAM, "flash" memory (e.g., NAND/NOR), and PSRAM.

As used herein, the terms "microprocessor" and "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, reconfigurable compute fabrics (RCFs), array processors, secure microprocessors, and application-specific integrated circuits (ASICs). Such digital processors may be contained on a single unitary IC die, or distributed across multiple components.

As used herein, the terms "network" refers generally to any type of telecommunications or data network including, without limitation, hybrid fiber coax (HFC) networks, satellite networks, telco networks, and data networks (including PANs, MANs, WANs, LANs, WLANs, piconets, micronets, internets, and intranets). Such networks or portions thereof may utilize any one or more different topologies (e.g., ring, bus, star, loop, etc.), transmission media (e.g., wired/RF cable, RF wireless, millimeter wave, optical, etc.) and/or communications or networking protocols (e.g., SONET, DOCSIS, IEEE Std. 802.3, ATM, X.25, Frame Relay, 3GPP, 3GPP2, WAP, SIP, UDP, FTP, RTP/RTCP, H.323, etc.).

As used herein, the term "network interface" refers to any signal, data, or software interface with a component, network or process including, without limitation, those of the Firewire (e.g., FW400, FW800, etc.), USB (e.g., USB2), Ethernet (e.g., 10/100, 10/100/1000 (Gigabit Ethernet), 10-Gig-E, etc.), MoCA, Serial ATA (e.g., SATA, e-SATA, SATAII), Ultra-ATA/DMA, Coaxsys (e.g., TVnet™), radio frequency tuner (e.g., in-band or OOB, cable modem, etc.), WiFi (802.11a,b,g,n), WiMAX (802.16), PAN (802.15), or IrDA families.

As used herein, the term "signal" refers to any electrical, optical, electromagnetic, subatomic, thermal, chemical/electro-chemical, or other transferal of information. Such signal may be, without limitation, in the analog or digital domain, or otherwise. Specific examples of signals include waveforms, pulses, binary digital data, analog voltage levels, modulated radio or infrared waves, including temporal and/or spatial variations of any of the foregoing.

As used herein, the term "storage device" refers to without limitation computer hard drives, DVR device, memory, RAID devices or arrays, optical media (e.g., CD-ROMs, Laserdiscs, Blu-Ray, etc.), or any other devices or media capable of storing content or other information.

As used herein, the term "user interface" refers to, without limitation, any visual, graphical, tactile, audible, sensory, or other means of providing information to and/or receiving information from a user or other entity.

As used herein, the term "wireless" means any wireless signal, data, communication, or other interface including without limitation WiFi, Bluetooth, 3G, HSDPA/HSUPA, TDMA, CDMA (e.g., IS-95A, WCDMA, etc.), FHSS, DSSS, GSM, PAN/802.15, WiMAX (802.16), 802.20, narrowband/FDMA, OFDM, PCS/DCS, analog cellular, CDPD, satellite systems, millimeter wave or microwave systems, acoustic, and infrared (i.e., IrDA).

Overview

In one fundamental aspect, the present invention comprises methods and apparatus for utilizing phonocardiography or "heart sounds" in combination with one or more other techniques (for example, impedance cardiography or ICG waveforms, and/or electrocardiography or ECG waveforms) to provide more accurate and robust physiological and/or hemodynamic assessment of living subjects. In effect, one exemplary implementation of the invention utilizes an ensemble of hemodynamically significant (or potentially significant) events to better, inter alia, identify fiducial points and assess cardiac and hemodynamic system function.

In one variant, the aforementioned methods and apparatus are used to improve ICG fiducial point (e.g., so-called B, C and X point) detection and identification accuracy. Moreover, the new ICG fiducial points that may be clinically important may be identified using the disclosed methods and apparatus.

In another aspect, the combination of heart sounds with ICG and/or ECG signals is used to better identify and assess hemodynamic information (such as PEP (pre-ejection period), LVET (left ventricular ejection time), Ejection Fraction, Regurgitation, conduction problems, valvular defects, stenosis, or reduced ejection fraction, etc.) through e.g., the use of the aforementioned improvements in fiducial point determination, and/or in the presentation of additional information that permits better classification of ICG waveforms obtained from the subject.

In a further aspect, the invention discloses methods and apparatus for utilization of ICG and/or ECG waveform information to improve the identification and characterization of heart sounds (such as e.g., S1, S2, S3, or S4 heart sounds), murmurs, and other such artifacts or phenomena.

In another aspect of the invention, the physiological process of regurgitation can be identified and/or assessed using the present invention. This provides a more accurate confirmation of the presence of regurgitation, or alternatively localizes where to look for the event.

In another aspect of the invention, the length (duration) of one or more heart sounds is determined and used for inter alia fiducial point or artifact/event identification or location.

In yet another variant, the duration of the heart sound(s) relative to QRS complex duration or length is evaluated. This approach gives information regarding the electrical activity of the heart relative to its aural activity. Moreover, the position of one or more ICG fiducial points within the heart sound(s) itself may be determined and evaluated.

While broadly applicable to many different types, species, conditions and dispositions of living subjects, the present invention finds particular utility with respect to monitoring more degraded heart failure patients where the blood flow hemodynamic properties may be very different (and often more challenging to detect and interpret) than those of normal, healthy patients.

Description of Exemplary Embodiments

Exemplary embodiments of the present invention are now described in detail. It is noted that while the exemplary embodiments of the invention is described herein in terms of an apparatus and methods for determining, inter alia, fiducial points and non-invasive hemodynamic measurements (e.g., cardiac output) suitable for use on the thorax of a human subject, the invention may also be embodied or adapted to use at other locations on the human body, as well as on other warm-blooded species such as, for example, primates, canines, or porcines. All such adaptations and alternate embodiments are considered to fall within the scope of the claims appended hereto.

Methods

The methodology of the present invention generally involves using one source of physiological data (and features or events associated therewith) to corroborate or detect other features or events in other sources of data, thereby enhancing the robustness and accuracy of the overall measurement(s).

FIG. 1 illustrates this generalized methodology graphically. In one specific embodiment of the method 100 (see FIG. 1a), the ECG "R" marker is used as a reference for confirming the timing of S1 and S2 heart sounds. As is well known to those of ordinary skill in the art, the S1 and S2 heart sounds correspond to aortic valve opening and closing, which are also associated with the "B" point and the "X" point in the ICG waveform. Since the B and X points are used in ICG techniques to determine hemodynamic parameters, by using the very reliable ECG "R" point to more reliably detect and/or validate S1 and S2 heart sounds, and then by using these sounds to more accurately detect X and B points in the ICG waveform, then the hemodynamic parameters can be determined more accurately.

As shown in FIG. 1, the generalized method 100 comprises first obtaining a waveform from the subject (step 102). In the present embodiment, this comprises an ECG waveform, although it will be appreciated that other waveforms may be used depending on context.

Next, one or more markers or features (e.g., R point) is identified within the obtained waveform per step 104.

Per step 106, the identified marker(s) is used to evaluate, confirm, or validate the timing of other data. In the present embodiment, the other data comprises phonocardiographic data (e.g., heart sounds) having S1 and S2 events (or sub-portions or features thereof), and the R point is used to validate the timing of these S1 and/or S2 events. S1 and S2 detection algorithms are known in the art; see, e.g., the technology set forth in U.S. Pat. No. 7,096,060 to Arand, et al. issued Aug. 22, 2006 and entitled "Method and system for detection of heart sounds", incorporated herein by reference in its entirety. Accordingly, such algorithms are not described further herein.

In one embodiment, the S1 sound is of particular interest (due in large part to its coupling to the opening of the aortic valve).

Once the timing of the events has been validated, the validated sound(s) is/are used to detect or evaluate one or more features or artifacts in another waveform (e.g., the B and X fiducial points within the ICG waveform) per step 108. Any number of different mechanisms for fiducial point detection may advantageously be used consistent with the present invention; see e.g., U.S. Pat. No. 6,561,986 issued May 13, 2003 entitled "Method and Apparatus for Hemodynamic Assessment including Fiducial Point Detection", incorporated herein by reference in its entirety, for one such exemplary technique.

In another variant of the method, the first waveform of step 102 above (e.g., the ECG signal) is used to first locate the "R" point reference; this information is then used to identify S1 and/or S2 heart sounds from the phonocardiographic data. These S1 and S2 heart sounds may not be able to be otherwise reliably identified due to, e.g., ambient noise or waveform corruption. However, by using the R point or other fiducial reference having a known correlation with the sounds, the identification of the S1 and S2 sounds achieves a much higher level of confidence. This can also lead to higher confidence in other heart sounds such as e.g., murmurs, or S3 and S4 heart sounds.

Accordingly, one embodiment of the invention comprises generating a confidence measure or parameter using the R point technique described above to indicate to a clinician or caregiver (or even an algorithm or automated system) when the sounds are reliably detected. It will be appreciated that this confidence measure may comprise any number of forms, such as for example and without limitation: (i) a "go/no-go" parameter or gating criterion; (ii) a metric (e.g., "percent confidence") which merely advises the clinician or caregiver as to the relative confidence level of the measurement; (iii) an input to an analysis or evaluation algorithm which uses this information along with other data to arrive at a derivate quantity or recommendation; and/or (iv) an input to a historical, anecdotal or other database such as for "matching" of the detected data to one or more patterns or templates as an aid to classification or recognition. The confidence measure (or any derivative parameters) may be a linear or non-linear quantity, or may utilize a fuzzy logic or other such approach (e.g., "low confidence", "moderate confidence", "high confidence") of the type well known in the signal processing arts. In another embodiment, the relative or absolute "quality" of data (e.g., a beat) can be assessed, and this information can be used for any number of purposes such as e.g. (i) selection or replacement of a reference beat (i.e., one that is used as a standard or reference for other measurements or comparisons); and (ii) determining whether a given data (e.g., beat) is suitable to be included within an ensemble average or other such technique which uses two or more beats.

In one embodiment of the invention, cardiac waveforms obtained from a subject may be processed using techniques generally associated with bigeminy and trigeminy processing and evaluation. As is well known, bigeminy is a condition wherein premature beats of the heart alternate (typically regularly) with normal beats. Generally harmless, bigeminy is generally either atrial or ventricular in nature, depending upon whether the alternating premature beats are atrial or ventricular. In cases where the premature beats alternate regularly, bigeminy sounds in effect like a "regularly irregular" heart rhythm.

Similarly, so-called "trigeminy" comprises another abnormal but usually harmless rhythm. In trigeminy, one ventricular premature complex (VPC) occurs after every two normal QRS complexes (hence the term "tri"). Note that in this trigeminic rhythm, two VPCs never occur sequentially (i.e., one after the other). See, e.g., U.S. Pat. No. 7,146,206 to Glass, et al. issued Dec. 5, 2006 entitled "Detection of cardiac arrhythmia using mathematical representation of standard ARR probability density histograms", incorporated herein by reference in its entirety, for one example of bigeminy/trigeminy processing techniques useful with the present invention.

Hence, in the current embodiment of the invention, waveforms obtained from the subject can be electronically parsed into two or more "bins" so that they may be evaluated, and classified/treated differently if desired. This "binning" could be accomplished for example by identifying uniquely repetitive classes of heartbeats. For instance, heartbeats may have different, unique repetitive relationships between the electrical conduction characteristics (as modeled by ECG) and the mechanical beat/flow characteristics as modeled by impedance (e.g., ICG). This type of processing by separation could improve accuracy, and also advantageously avoids possible errors or misdiagnoses. This functionality may be user-configurable or selectable as well. For example in one variant of the invention, a waveform processing algorithm is adapted to evaluate the shape of successive beats or artifacts in the waveform(s) being processed, and segregate them into separate processing bins. Alternatively, the user (e.g., physician, etc.) may view the waveform and utilize their intrinsic knowledge and skill to recognize the various different types of shapes or artifacts, and segregate them accordingly (such as via a PC or touch-screen user interface, such as a GUI) that allows the user to readily select or classify different types of artifacts they see). In many cases, the human eye/mind is much more efficient at recognizing patterns (especially some that may be somewhat subtle), and can also advantageously make "judgment calls" on beats or artifacts which are not clear cut.

It will also be appreciated that the foregoing approach affords the clinician, in certain circumstances, the ability to look at cardiac outputs for two or more different conduction paths/modes. Many prior art systems effectively presume the existence of one conduction path through the thorax/cardiac muscle, or at least aggregate the data (which may have components of multiple conduction paths inherent therein). In contrast, the aforementioned embodiment of the present invention allows for intelligent parsing or separation of data from different conduction paths, and evaluation thereof. More specifically, different electrical conduction paths for the heart muscle may be identified by the fact that they produce very different impedance waveforms, and valve timing as characterized and confirmed by ICG and by heart sounds relative to the ECG waveform characteristics. In one exemplary embodiment of the invention, an ECG waveform (indicative of inter alia the electrical activity of the heart) is obtained. The mechanical aspects of the heart's operation are then evaluated (e.g., via impedance or ICG), including for example evaluating changes in the ICG. Additionally, the timing of the heart valves can also be determined via heart sounds monitoring. By evaluating all of this data (ECG, ICG and heart sounds) in concert, valuable insight into different electrical conduction paths through the heart muscle are obtained. For example, one conduction path might yield a very different ECG/ICG/heart sounds composite "profile" than another conduction path, and/or the relationship of the various data to each other (e.g., relative timing, amplitude, etc.) may vary across different conduction paths. Hence, in one respect, the present invention allows for a more detailed profile of the heart in terms of electrical, mechanical and auditory activity, which may vary across different conduction paths.

The heart sounds-validated beats can also be differentiated from those not obtained or validated by way of heart sounds data (such as by forming two classes of beats, with each class processed separately). Alternatively, beats that do not have the benefit of "full" processing (i.e., use of R point in ECG to validate heart sounds data, and then using this data to obtain or validate B, C or X points) can be identified or segregated from those which do have full processing. Myriad other ways of using quality or confidence assessments relative to the obtained cardiac data will be recognized by those of ordinary skill given the present disclosure.

Moreover, When the S1 and S2 sounds are "confidently" identified (for example, with the confidence metric exceeding a prescribed condition or value), they can be used to identify one or more ICG waveform characteristics or features that correspond to other events. For example, the S1 and S2 sounds can be correlated to the aforementioned ICG "B" and "X" points, which are typically associated with the aortic valve opening and closing, respectively. Hence, by uniquely knowing the ICG waveform characteristics that relate to aortic valve opening and closing, ICG signals can more reliably identify the B and X points, and thereby more accurately determine a variety of hemodynamic parameters.

It will be recognized that the foregoing confidence measure or parameter(s) can also be extended to the B and X point determinations, and even the hemodynamic parameters if desired. Much as one weak link affects the overall strength of a chain, a low-confidence S1 and/or S2 detection can adversely affect the confidence level of the B and/or X point determinations, and hence any derivative or subsequent determination (such as e.g., cardiac output). Conversely, through use of the techniques of the present invention, the S1 and S2 sounds can be more reliably determined (since they are correlated to a known reference), and hence any derivative or subsequent determinations based on these "improved" S1 and S2 sounds will benefit accordingly, and this can be represented numerically, heuristically, or in another fashion to the clinician.

This also underscores one salient benefit of the techniques described herein; i.e., an increase in the clinical "robustness" of the system. Specifically, under prior art approaches, low confidence in one or more parameters (such as B or X point) necessarily provides a "weak link" in the ICG chain by reducing the confidence in the calculated cardiac output (CO). However, by more accurately determining (or simply validating the determination of) the B and X points, the confidence in the CO measurement is also improved. Stated differently, the determination of B and X points can be more tenuous (whether due to noise, difficult-to-evaluate waveforms of certain patients, etc.), since the R-point confirmed heart sounds will aid in reliably pulling these points "out of the noise". Without the S1 and S2 information, prior art solutions can tolerate less noise, interference, or waveform anomaly since there is no complementary source of information.

Similarly, heart sounds can often be obscured by internal or external acoustic or other noise sources, and hence are not always a reliable indicator. Therefore, the present invention contemplates that there may be times when the heart sounds information is not available (or cannot be confidently determined, even with the aforementioned ECG R point reference), at which point the use of this data is suspended for a period of time, and/or until its confidence level increases. Again, the system is more clinically robust, since its output is not wholly dependent on one parameter or the other; they each rather act in concert to enhance the confidence of the resulting measurement, but are alone may not be individually critical to the measurement.

It will also be appreciated that the foregoing parameters and characteristics may be markedly different in different subjects; hence, the techniques of the present invention advantageously afford the ability to uniquely "fingerprint"

each individual measured. Specifically, by using the R point of a particular individual to determine (with good confidence) the occurrence of the S1 and/or S2 sounds for that same individual, and using these sounds to enhance the confidence or reliability of the ICG waveform features of interest (e.g., B and X points) for that individual, a unique and high-confidence correlation between R point, S1/S2 sounds, and ICG B and X points is established for each subject. This data can also be stored for future reference, not only for use in treating that same subject irrespective of location (such as via transmission over the Internet or another network), but also as part of establishing a database of these correlations. Such a database might comprise, for example, other potentially relevant data for the individual (e.g., weight, height, age, body mass index, relevant conditions, medications at time the correlation was obtained, pulse rate, blood pressure, etc.), which enables either a human-based (physician) or algorithmic analysis of the data across multiple subjects to identify any statistically significant correlations therein. For example, it might be determined through analysis of this data for many individuals that certain ICG waveform characteristics become: more prominent, more reliable, time-shifted with respect to other events, and so forth as a function of age. Or, certain ICG or heart sounds characteristics may only present themselves in certain classes of patients (e.g., those with CHF, obese patients, patients with lung congestion, etc.). The foregoing processes may also be implemented in a dynamic fashion, thereby providing even greater adaptability and accuracy of the system. Specifically, the correlations, characteristics or references for a given individual may change as a function of time, condition, etc. For example, on one day, the reliable determination of S1 and S2 may yield a first set of ICG characteristics that help accurately determine B and X points. However, on a different day (same subject), other ICG characteristics may be more useful or reliable. Or, there may be marked changes between when that subject is waking and ambulatory versus sedated (such as when under anesthesia). Advantageously, the evaluation algorithms of the present invention can be made adaptive so that the model applied to each subject can be altered as a function of time or condition, so as to determine the optimal correlation. For example, in one variant of the algorithms, a first R point and S1/S2 correlation is made, from which a first B and X point identification is then made. As previously described, a confidence level can be ascribed to all or portions of this determination, so as to provide some basis for future comparison. After a period of time, the algorithm then repeats this process, identifying the R point and S1/S2 sounds again, and then again correlating to ICG characteristics for B and X point determination. However, if the confidence level of the second determination is better than the first, the algorithm may select the second set of data for subsequent use. In this fashion, the system is always attempting to improve the confidence level of its results by choosing a characteristic model or correlation that produces the best confidence. This "self healing" approach can be implemented based on any number of different logical schemes, such as averaging (e.g., take n samples and then average results, and compare to a subsequent average of n different samples), trend (e.g., if n successive subsequent determinations provide increased confidence, use one or both of the subsequent determinations over a prior one), and the like.

Use of heart sounds in combination with ICG waveforms and ECG waveforms also advantageously facilitates another capability; i.e., the identification of one or more new ICG fiducial points that may be clinically significant. For example, it may be determined that certain patients (or classes of patients) exhibit a certain artifact or feature which is not a B, C or X point per se, but none-the-less provides a useful reference for CO or other hemodynamic measurements. Such artifacts may not be a "peak" or "trough", but perhaps another shape or event of interest (e.g., inflection point, bump, irregularity, etc.). This detection or determination may be made for example algorithmically (e.g., via a computer program adapted to analyze and recognize certain wave shapes or features), or manually (e.g., by a trained physician), or both (e.g., via application software which allows a physician or other caregiver to review and assist in the identification and selection process). See the discussion of waveform assessment and shape analysis provided subsequently herein.

Yet another benefit of combining ICG, ECG and heart sounds data according to the exemplary embodiment described above is that the information from these different monitoring modalities can be used in complimentary ways to identify patient conditions that may need attention. For example, in one variant, if the monitored heart sounds contain the presence of an "S3" or "S4" heart sound, which may be indicative of a left ventricular failure (S3), or myocardial infarction (i.e., heart attack) or shock (S4), as previously described. This information may be combined with (or evaluated in light of) the ICG and/or ECG characteristics and interpretations (such as for example ST segment depression or elevation and suspected presence of t-wave alternans, which act as "flags" for the presence of certain conditions), to more definitively diagnose and evaluate a patient's condition. Hence, the presence of an S3 or S4 sound can in one embodiment be used as a threshold or triggering event for more detailed analysis of the corresponding ICG and/or ECG data, such as via an algorithm. Alternatively, this could cause the physician to have the subject perform physical movement or a maneuver (such as bending over at the waist, rolling on their side, standing up, sitting down, exercising, etc.). See e.g., the exemplary logical flow of FIG. 1a, wherein the presence of S3 or S4 can be used to institute a logical process by which other data sources (e.g., ICG and/or ECG) can be used to confirm the presence of a given condition (or demonstrate the presence of correlations within the different sources, which can then be used as an input to a recognition or diagnostic algorithm).

In another variant, clinical testing performed by the Assignee hereof has produced ICG waveform data that shows characteristics that are believed to be associated with regurgitation of blood from poor heart muscle performance. Heart sounds can contain acoustic "murmur" information that augments and can be used to confirm this association, and make the detection of this murmur condition more reliable. As previously described, this measurement can also advantageously be used to optimize pacemaker settings of AV and VV timing for optimal heart muscle performance; see, e.g., U.S. patent application Ser. No. 10/453,820 filed Jun. 2, 2003 entitled "Physiologic Stimulator Tuning Apparatus and Method", previously incorporated herein.

In another embodiment of the invention, selective event or data screening or rejection can be applied to the heart sounds, ICG, and/or ECG signals in order to add additional clinical robustness. See, e.g., co-owned and co-pending U.S. patent application Ser. No. 10/995,920 filed Nov. 22, 2004 entitled "Method and Apparatus for Signal Assessment Including Event Rejection", incorporated herein by reference in its entirety, which discloses a method of assessing physiologic (e.g., hemodynamic) parameters within a living subject through analysis of continuous or non-continuous waveforms, including artifacts within these waveforms. This assessment includes enhanced or "intelligent" rejection of certain portions of the waveform(s). By accurately rejecting or not rejecting these portions of the analyzed signals, greater accuracy and clinical robustness are provided. Furthermore, a greater level of confidence in the physiologic data obtained (or data derived therefrom) is also provided through use of this approach.

Moreover, various waveform assessment techniques may be used consistent with the present invention to inter alia more accurately determine fiducial points, and enhance the clinical robustness of the system. See, e.g., U.S. Pat. No. 7,043,293 issued May 9, 2006 and entitled "Method and Apparatus for Waveform Assessment", incorporated herein by reference in its entirety, which discloses methods and apparatus for detecting artifacts or features with one or more time-variant information streams (e.g., waveforms). In an exemplary embodiment adapted for use in identifying (and utilizing) artifacts in the cardiograms of a human subject, the invention comprises computer code running on a digital processor which is adapted to analyze the subject's ECG waveforms to identify atrial and ventricular pacing spikes. When these spikes are detected, they may substitute as Q points during definition of the AZ search interval for B, C, and X points in a thoracic impedance waveform. Such searches may be conducted using, for example, the wavelet transform model described in co-pending and co-owned U.S. Pat. No. 6,561,986 entitled "Method and Apparatus for Hemodynamic Assessment including Fiducial Point Detection" previously incorporated herein. Pacing spike detection in the aforementioned exemplary application incorporates some aspects of artificial intelligence, in that it is desirable to detect spikes of varying amplitude, with variable time delays between the A and V spikes, in the presence of noise also having a variable amplitude. This is accomplished using a golden section search optimization technique, in conjunction with a fuzzy model. The golden section search identifies spikes or other artifacts based primarily on their shape as opposed to amplitude or other criteria, thereby significantly increasing the robustness of the detection algorithm.

In another aspect of the invention, the physiological process of regurgitation can be identified and/or assessed using the present invention. In one embodiment, an ensemble of indicia (including for example the ECG and ICG waveform, and heart sounds) is used to more accurately confirm the presence of regurgitation, or alternatively localize where to look for the event. More specifically, in one embodiment, unique ICG waveform characteristics that have been clinically identified to be likely indicative of regurgitation can be correlated with expected heart sound murmurs. This murmur confirmation may allow physicians to more reliably identify dangerous or undesirable heart conditions. This capability may be especially useful in, inter alia, pacemaker applications where adjustment of the AV or VV (or both) settings of the pacemaker is being conducted, such as for resynchronization of the heart. Exemplary pacemaker tuning and assessment methods and apparatus are described in co-owned and co-pending U.S. patent application Ser. No. 10/453,820 entitled "Physiologic Stimulator Tuning Apparatus and Method" filed Jun. 2, 2003, which is incorporated herein by reference in its entirety, although it will be appreciated that other methods and apparatus may be used consistent with the present invention with equal success.

In another aspect of the invention, the length (duration) of one or more heart sounds is determined and used for inter alia fiducial point or artifact/event identification or location. This duration can be readily determined by, for example, measuring amplitude as function of time, and then measuring the duration from the onset point (i.e., where amplitude is a prescribed frequency or set of frequencies increases significantly or above a prescribed threshold value) to the termination point (i.e., where the amplitude decreases significantly or to below a threshold value). Other schemes for measuring duration may be used as well.

In another variant, the duration of the heart sound(s) relative to QRS complex duration or length is evaluated. This approach gives information regarding the electrical activity of the heart relative to its aural activity. Moreover, the position of one or more ICG fiducial points within the heart sound(s) itself may be determined and evaluated.

Unified Sensor Apparatus

Figure 2A:
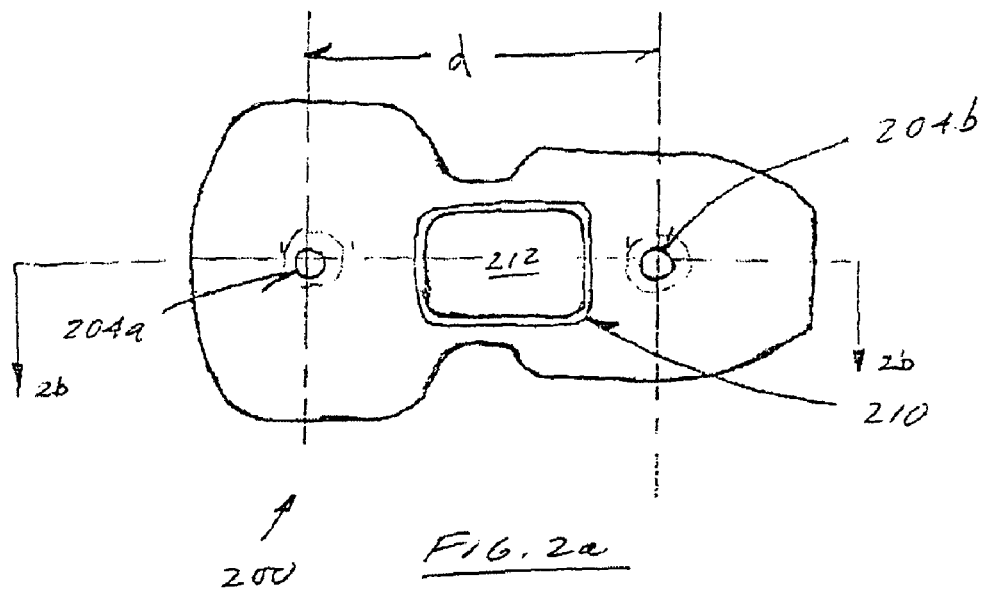
FIG. 2a is a top elevational view of one embodiment of a disposable sensor apparatus with unified detection capability according to the present invention.
Figure 2B:
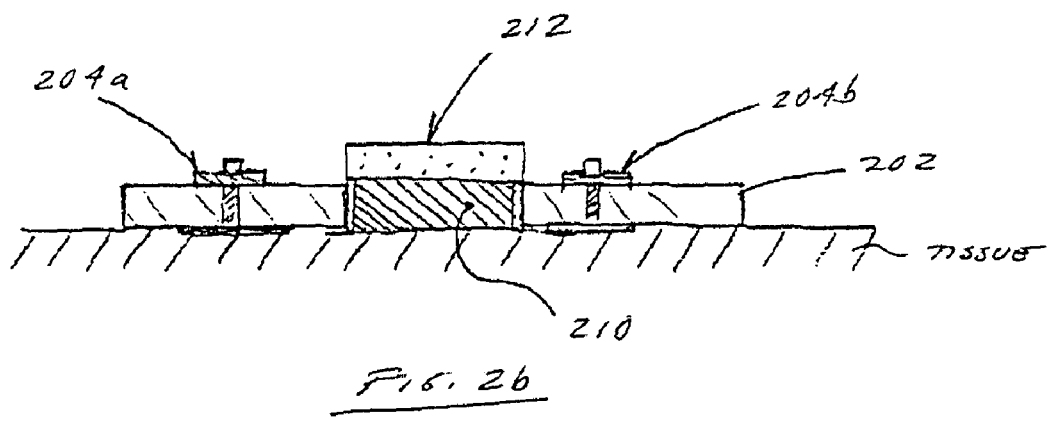
FIG. 2b is a cross-sectional view of the sensor of FIG. 2a, taken along line 2b-2b, showing the details thereof.

In another salient aspect of the invention, an improved sensor apparatus is disclosed. FIGS. 2a and 2b illustrate one exemplary embodiment of the sensor according to the present invention. In this embodiment, the sensor 200 comprises a disposable sensor generally similar to those utilized for ICG measurements, although this is not a requirement. One such exemplary electrode configuration is shown in U.S. Pat. No. D475,138 issued May 27, 2003 entitled "Electrode for Use on a Living Subject", incorporated herein by reference in its entirety. See also U.S. Pat. No. D471,281 issued Mar. 4, 2003 of the same title, also incorporated herein by reference in its entirety. Unlike a conventional ICG electrode, however, the exemplary disposable sensor of FIGS. 2a-2b combines the ability to detect heart sounds, ICG and ECG, all via the same sensor 200. As shown, this embodiment of the sensor 200 comprises a patch like substrate 202 with two terminals 204a, 204b. The terminals may have a predetermined centerline terminal spacing (d in FIG. 2a) if desired, such as according to the teachings of U.S. Pat. No. 6,636,754 Oct. 21, 2003 entitled "Apparatus and Method for Determining Cardiac Output in a Living Subject", incorporated herein by reference in its entirety. The sensor 200 also optionally utilizes an asymmetric terminal size, such that one terminal 204a is smaller than the other 204b. Note that the different sized terminals provide utility in the use of the sensors to assure proper device connection.

Additionally, the sensor 200 comprises a chamber 210 for coupling acoustic emissions (e.g., heart sounds) to an external device as discussed subsequently herein. In one variant, the chamber 210 comprises an acoustic condenser or focusing /amplification mechanism of the type well known in the acoustic arts. The chamber is centrally located, and coupled to the surface of the tissue of the subject (see FIG. 2b) so as to channel acoustic energy to a receptor device 212 disposed atop or proximate the chamber 210. In one embodiment, the receptor comprises a piezoelectric device (i.e., one that generates a potential as a result of applied pressure oscillations such as sound) of the type well known in the arts. In another embodiment, the sensor comprises a piezoresistive device; i.e., one whose resistance varies as a function of pressure. Myriad other well known technologies for receiving acoustic energy will be recognized by those of ordinary skill (e.g., a diaphragm with attached coil, microphone, etc.), such technologies also being useful with the invention.

The aforementioned sensor 212 may also be fitted with an electrical or data interface (described below) of various types so as to permit the acoustic data to be transmitted to an external or host device such as an ICG module or the like. See, e.g., the exemplary module and other technology described in U.S. Pat. No. 6,602,201 issued Aug. 5, 2003 entitled "Apparatus and Method for Determining Cardiac Output in a Living Subject", incorporated herein by reference in its entirety, for one exemplary ICG module configuration useful with the present invention. In one embodiment, a single lead is utilized to interface between the disposable sensor and the host device. In one exemplary configuration, the connector used for each lead comprises a simplified electrical connector of the type generally described in co-owned and co-pending U.S. Pat. No. 7,214,107 to Powell, et al issued May 8, 2007 entitled "Electrical Connector Apparatus and Methods", incorporated herein by reference in its entirety, although any number of other different connector configurations may be used.

One approach for the unified sensor implementation 200 comprises use of the same signal line(s) for the ICG, ECG and heart sounds signals, thereby obviating additional signal paths. These signals are separated via any number of different well-known techniques such as e.g., via frequency characteristics, and/or with signal separation algorithms. For example, in one embodiment, the ECG signals are in the frequency range of 0.05 Hz to 120 Hz, while S1 and S2 heart sounds have similar frequency characteristics in the range of about 20-150 Hz. However, ICG is usually measured at much higher frequencies around 70 khz, and this difference can be used as a basis for separation. This approach advantageously allows for the use of a single electrical interface (e.g., connector) as previously described. The signals from the acoustic sensor element 212 may be detected through the same connections as used for the ECG and ICG signals. As another approach, the disposable heart sound, ECG and ICG sensor 200 may be used with one or more additional leads so the heart sounds and the ECG signals can be separated in frequency.

In another variant of the invention, a cable used to transfer signals from/to the sensor 200 also includes the piezoelectric/piezoresistive device or microphone integral therein, thereby further reducing the cost of the disposable sensor. For example, the chamber 210 of this variant may have a receptacle or aperture formed therein, where the cable (with acoustic sensor) can be plugged into. When monitoring is complete, the cable and acoustic sensor 212 are retracted, and can be re-used, while the sensor 200 is merely disposed of.

In another embodiment, a substantially unified connector may be used with the sensor 200, so as to obviate having to individually place or connect two or more signal leads as in the prior art. For example, in one variant, a unified connector that allows simultaneous attachment to (i) both of the terminals 204a, 204b of the sensor 200; and (ii) a separate electrical interface for the acoustic sensor 212, is provided. This unified connector may also be polarized (i.e., only fits on one way, so as to accommodate the differently sized terminals 204 as previously described. In another variant, the analog signals of the sensor 212 are routed to one or the other (or both) of the ECG/ICG terminals, and hence the unified connector need only support two electrical interfaces (one for each terminal 204).

In another embodiment, the unified connector can include within it the acoustic sensor or microphone 212, so that when the connector is plugged or mated onto the sensor 200, the acoustic sensor 212 is mated up with a receptacle or acoustic channel, thereby allowing for clear reception of heart sounds. Likewise, when the unified connector is removed, the acoustic sensor or microphone 212 travels with the connector.

Alternatively, a traditional signal cable arrangement can be used for the ECG/ICG signals obtained from the terminals 204 of the sensor 200, while a separate wired or wireless interface can be used to transmit the heart sounds signals. For example, in one variant, low cost RFID (radio frequency ID) technology of the type well known in the art can be used to transmit data from the sensor 200 to a remote device. As is well known, such RFID devices may be active (i.e., internally powered) or passive, and may also backscatter energy in a modulated fashion. Hence, in one configuration, the sensor 200 is adapted to backscatter modulate an interrogation signal, the modulation comprising data obtained from the analog heart sounds sensor 212, which is converted to the digital domain via an A/D converter (not shown). In this fashion, the RFID device (which may be very small, and embedded within the sensor patch 202 or other component if desired) can generate a binary data stream that is transmitted off-sensor with no wires and no requirement for indigenous power. However, active RFID devices may also be used consistent with the invention if desired.

In yet another embodiment, a capacitive or inductive data interface of the type well known in the art is used, so as to permit wireless transfer of data from (and to) the sensor 200. For example, one variant of the sensor comprises a capacitive interface, wherein the position of a first at least partly conductive surface or membrane (disposed on the sensor 200) is varied or modulated by the action of the acoustic heart sounds. A second surface or membrane, associated with the cable or unified connector as previously described for example, is placed in close proximity to the first surface, with air or another material acting as a dielectric between the two surfaces. As is well known, the variation of spacing between the two at least partly conductive surfaces will cause a variation in the capacitance of the assembly, and this variation or modulation of capacitance can be used to generate an electrical signal to carry information to the host device as previously described. Similarly, the variation of an inductive coil or other such apparatus may be used to transfer information.

In yet another embodiment, a technology that replaces air pressure changes with electric field changes may be used. See, e.g., the exemplary "electromagnetic diaphragm" developed and sold by Thinklabs Medical, LLC of Centennial, Colo. for one commercially available device that may be adapted for use herewith. In effect, diaphragm movement represented as an electrical signal can be amplified and processed. The resulting electrical signal has a high conformance with the air pressure changes at the diaphragm of a traditional stethoscope, ensuring that the electrical signal captures the authenticity of stethoscope sound. In one variant, the electromagnetic diaphragm (EmD) is coated internally with a conductive surface. Behind the diaphragm is situated a conductor (e.g., metal plate) which is charged with a voltage, thereby establishing an electric field behind the diaphragm. As the diaphragm moves, the voltage induced on the plate changes due to variation of the electric field intensity as a function of position. Such implementations advantageously produce a sound familiar to the clinician, yet amplified and processed to extract the optimal characteristics.

Figure 2C:
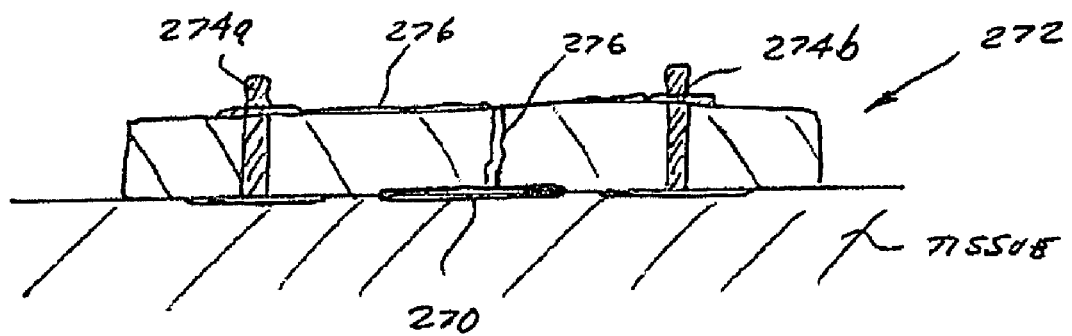
FIG. 2c is a cross-sectional view of another embodiment of the sensor of the invention, wherein a piezoelectric or piezoresistive film or layer is used.

In another embodiment (FIG. 2c), a thin-film piezoelectric or piezoresistive element 270 of the type well known in the art may be used to generate electrical signals relating to applied sound waves (e.g., heart sounds). As is known, such devices alter their electrical output or resistance, respectively, as a function of applied pressure (variations). Such devices may be made quite small and thin, and even for example disposed on or formed as a film or layer. Such film or layer can be used with the ICG/ECG patch 272 described elsewhere herein in one embodiment (and even utilize the existing electrical terminals 274a, 274b and leads if desired, such as via conductors 276 which are routed from the piezoresistive or piezoelectric element 270), thereby making a small form factor integrated device. Alternatively, the film or layer can be used as part of a separate device which may be applied at a close-by or different location as needed.

Also, in another variant, the sensor is equipped with a low cost buffer memory (not shown) that allows acoustic data that has been digitized to be stored and subsequently read out (e.g., "bursted") when a communication channel is established, such as when a reader wand or probe is passed over the sensor 200, or when the sensor comes in sufficient proximity of a reader device. The sensor could also work with, and require the connector to form a detector.

It will be recognized that while exemplary embodiments of apparatus and methodology are described herein in terms of the cardiac output determination, the invention also be readily used in assessing other hemodynamic parameters, such as without limitation the pre-ejection period (PEP, the interval between Q point and B point), isovolumetric relaxation time, presence of excess intravascular fluid, presence of excess pulmonary fluid and the like, and accordingly is not limited to the measurement of stroke volume, cardiac output, or QRS complex identification.

Apparatus for Hemodynamic Assessment

Figure 3:
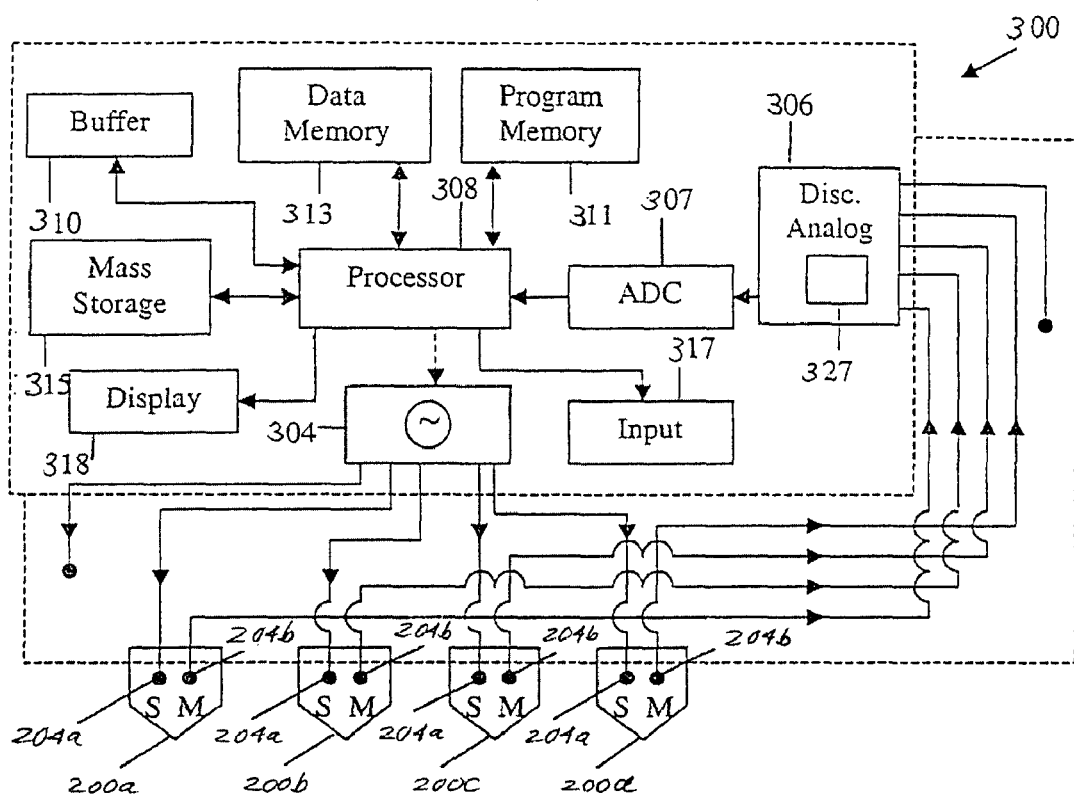
FIG. 3 is a block diagram of one exemplary embodiment of the apparatus for hemodynamic assessment according to the invention.

Referring now to FIG. 3, an apparatus for measuring hemodynamic properties associated with the cardiovascular system of a living subject is described. In the illustrated embodiment, the apparatus is adapted for the measurement of the cardiac output of a human being, although it will be recognized that other hemodynamic parameters and types of living organism may be evaluated in conjunction with the invention in its broadest sense.

The exemplary embodiment of the apparatus 300 of FIG. 3 fundamentally comprises a plurality of electrically conductive sensors or electrodes 200 (with individual terminals 204a, 204b) of the type described herein with respect to FIGS. 2a-2b for supplying a current and measuring voltage (and impedance) from the subject non-invasively; a current source 304 coupled to at least a portion of the electrodes 200 for providing the alternating (AC) electrical current supplied to the subject; discrete analog circuitry 306 for preconditioning the analog impedance and ECG waveforms derived from the electrodes 302, an analog-to-digital converter (ADC) 307 for converting the conditioned analog signals to a binary digital format; a digital processor 308 operatively connected to the ADC 307 for analyzing the digital representations of the conditioned ECG and impedance waveforms; a buffer memory 310 for storing conditioned data prior to fiducial point detection; program and data memories 311, 313, for storing program instructions and data, respectively; a mass storage device 315, an input device 317 for receiving operation command and data from the apparatus user, and a display device 318 for displaying information such as data and waveforms, as well as applications program interface, to the user. One or more algorithms (e.g., computer programs or code) used for, inter alia, the aforementioned analysis of the ECG, impedance, and/or heart sounds waveforms are disposed on the apparatus as well, such as being stored on a mass storage device (e.g., HDD), loaded into program memory of the digital processor 308, etc. Many functions may be implemented in firmware or even hardware if desired, as will be appreciated by those of ordinary skill in the computer arts. See also the discussion of exemplary computer programs provided subsequently herein.

The electrodes 200 of the embodiment of FIG. 3 comprise so-called "spot" electrodes of the type well known in the medical arts, although it will be recognized that other types of electrodes, including band electrodes may be substituted. As used herein, the term "spot" electrode includes both single- and multi-terminal electrodes adapted for use in a localized area of the subject's physiology, such as e.g., those of FIGS. 2a-2b.

In operation, the apparatus 300 generates an effectively constant current (via the current source 304) or constant voltage which is applied to certain ones of the terminal(s) 204 of the electrodes 200. The applied current derived from the current source 304 is a 70 kHz sine wave of approximately 2.5 mA maximum RMS. The measured voltage associated with the aforementioned sine wave is on the order of 75 mV maximum RMS. These values are chosen to advantageously minimize electric shock hazard and provide adequate signal to noise characteristics, although it will be appreciated that other frequencies, currents, or voltages may be substituted. The construction and operation of AC current sources is well known in the electronic arts, and accordingly is not described further herein.

The preprocessor 306 and associated signal processing apparatus is in electrical communication with other electrodes 200, from which potentials (voltages) are measured. In the selected frequency range of the AC signal (e.g., 70 kHz), the typical impedance associated with a human subject's skin is 2 to 10 times the value of the underlying thoracic impedance $Z_T(t)$. To aid in eliminating the contribution from skin and tissue impedance, the apparatus of the present invention uses at least two, and typically four electrode arrays 200a-200d for measurement, as shown in FIG. 3. In a simple application, one electrode array 200a comprising a stimulation electrode terminal 204a and a measurement electrode terminal 204b is applied above the thorax of the subject, while a second electrode array 200b (similarly having a stimulation electrode terminal and measurement electrode terminal) is applied below the thorax. The AC current (or pulsed waveform, or DC current, or another waveform shape such as sawtooth, square, NRZ, etc.) from the current source is supplied to the stimulation electrode terminals. Current flows from each stimulation electrode terminal 204a through each constant skin impedance, $Z_{sk1}$ or $Z_{sk4}$, each constant body tissue impedance, $Z_{b1}$ or $Z_{b1}$, and each constant skin impedance, $Z_{sk2}$ or $Z_{sk3}$, to each measurement electrode terminal 204b. The voltages at the measurement electrode terminals 204b are measured and input to a differential amplifier circuit 327 within the preprocessor 306 to obtain the differential voltage, $V_T(t)$. The desired thoracic impedance, $Z_T(t)$, is then obtained using the relationship of Eqn. 1.

$$Z_T(t) = \frac{V_T(t)}{I_T(t)} \qquad \text{(Eqn. 1)}$$

As shown in FIG. 3, two sets of electrode arrays 200a-d may advantageously be used to monitor the impedance associated with the left and right portion of the thorax in the present invention. When eight electrode terminals (four arrays 200a-d each with two terminals 204a, 204b) are used in this manner, the four measurement arrays are also used to obtain an electrocardiogram (ECG). As previously discussed, the Q wave of the ECG QRS interval is used to, inter alia, determine the subject's heart rate, identify the QRS complex and Q and R points, and as an input to the fiducial point detection algorithm for the impedance waveform. Heart sounds information obtained from the sensors 200 (via acoustic sensors 212) is also passed via the electrical or wireless interface previously described to the apparatus 300 for processing as set forth above. In one embodiment, the heart sounds information is carried as electrical signals via the same conductors used for ICG/ECG signals. In another embodiment, the heart sounds information is carried via a separate set of electrical conductors. In yet another embodiment, the auditory signals generated by a transducer disposed on the subject being monitored are converted into electrical signals, which are then converted to electromagnetic radiation (e.g., radio frequency or IR) and sent over a wireless data link. In yet another embodiment, the auditory signals (pressure variations) are transmitted via an interposed medium (such as via an audio tube) to another component and then converted to electrical signals.

It will also be appreciated that the exemplary embodiments of the invention utilize data acquisition apparatus that provide simultaneous or near simultaneous data (or at least a chronological or other reference so that the various types of data can be properly synchronized with one another later on). Signals may optionally be, for example, indexed or referenced to a clock signal generated within the apparatus (such as by a crystal clock generator or the digital processor) and distributed to various components. Signal acquisition, transit and processing times may also need to be considered and accounted for (such as via, e.g., insertion of a positive or negative time index offset, so as to chronologically align the various data). Such techniques are well known to those of ordinary skill in the electronic and signal processing arts, and accordingly not described further herein.

It is noted that the apparatus 300 described herein may be constructed in a variety of different physical configurations, using a variety of different components, and measuring a variety of different hemodynamic parameters. For example, some or even all of the foregoing components may be physically integrated (such as in an application specific integrated circuit incorporating a DSP core, memory, "front" end analog processing, and ADC in a single piece of silicon), and/or the functionality associated with multiple components performed by a single multi-function component (e.g., a processor adapted to perform calculations associated with the wavelet transform methods disclosed herein, as well as host functions such as video display, bus arbitration, etc.). One exemplary configuration comprises a PC-based device of the type well known in the art, having a host microprocessor as well as the aforementioned preprocessing and signal processing functionality in the form of a separate DSP in data communication therewith. In yet another embodiment, the apparatus comprises a mobile personal computing device (such as a personal digital assistant, or PDA), which is adapted to receive input data from the electrodes 200 and analyze the data to produce a corrected measurement of cardiac output. It will also be recognized that other portable devices, such as laptop computers, calculators, and personal organizers, may conceivably be configured to run the computer program(s) of the present invention. Such portable devices are readily adapted to the methods of the present invention, since as a result of the invention's advantageous use of comparatively simple wavelet transforms, the processing and storage capability needed to implement the algorithm is decreased. Furthermore, a variety of different methods of transmitting the input sensor (i.e., electrode) data to these devices may be used, including networked computers, or even wireless data links as previously described.

Furthermore, cardiac output, LVET, SV, or other measurements generated by the foregoing apparatus 300 may also optionally be stored in the storage device 315 for later retrieval, or output to an external device such as a printer, data storage unit, other peripheral component via a serial or parallel port if desired. Furthermore, the apparatus 300 may be networked to another computing device or database (not shown) whereby the data generated by the apparatus may be remotely analyzed or stored. Transmission of output data to such remote devices may be accomplished using a variety of well understood methods, such as by local area network (LAN), intranet, Internet, fiber-optic systems, or radio frequency (wireless) devices.

It will be further recognized that while the apparatus 300 of the invention is described herein as a substantially discrete or "stand-alone" system, the invention may be adapted to act as a plug in card, module, or other complementary device (including any supporting software) for an existing ECG or patient monitoring system that utilizes electrodes. Hence, the invention can advantageously be "retro-fitted" to such prior art systems, thereby extending the utility of the pre-existing system, and potentially obviating the purchase of entirely new equipment.

Computer Program

A computer program for implementing the aforementioned methods of heart sounds, impedance and ECG waveform analysis is now described. In one exemplary embodiment, the computer program comprises an object ("machine") code representation of an assembly source code listing implementing the analysis methodologies previously described herein, either individually or in combination thereof. While assembly language is used for the present embodiment, it will be appreciated that other programming languages may be used, including for example VisualBasic™, Fortran, C, and C++. The object code representation of the source code listing is compiled and disposed on a media storage device of the type well known in the computer arts. Such media storage devices can include, without limitation, optical discs, CD ROMs, magnetic floppy disks or "hard" drives, tape drives, or even magnetic bubble memory. The computer program further comprises a graphical user interface (GUI) of the type well known in the programming arts, which is operatively coupled to the display and input device of the host computer or apparatus 300 on which the program is run.

In terms of general structure, the program is in one embodiment comprised of a series of subroutines or algorithms for implementing the methodologies described herein based on measured parametric data (e.g., the "input parameters" previously defined) which are provided to the host computer. In a second embodiment, the computer program comprises an assembly language/micro-coded instruction set disposed within the embedded storage device, i.e. program memory, of a digital signal processor (DSP) or microprocessor associated with the foregoing hemodynamic measurement apparatus of FIG. 3.

Method of Providing Treatment

Figure 4:
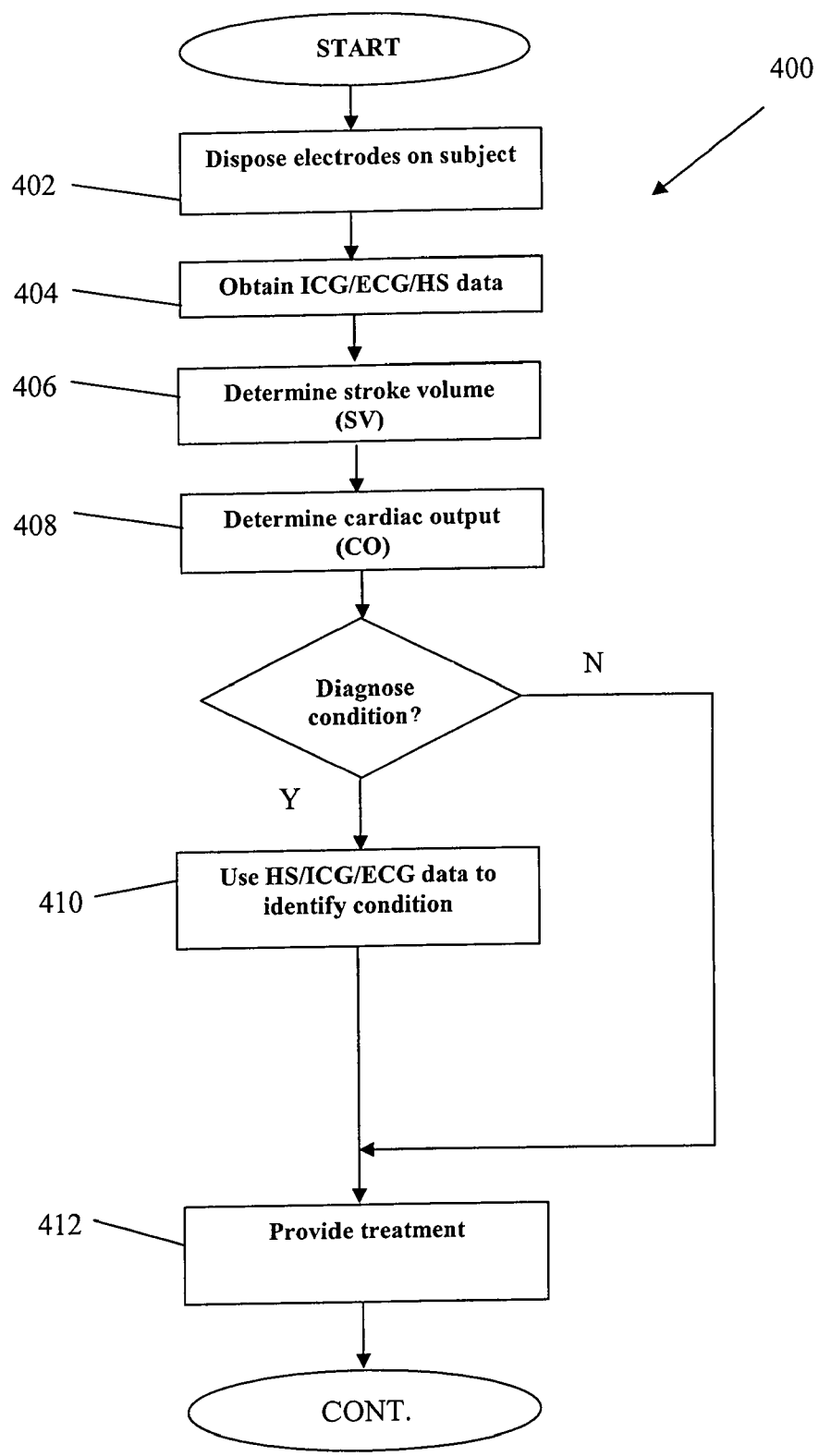
FIG. 4 is a logical flow diagram illustrating one exemplary embodiment of the method of providing treatment to a subject using the aforementioned methods and apparatus.

Referring now to FIG. 4, a method of providing treatment to a subject using the aforementioned methods is described. While the following discussion is cast in terms of the aforementioned methods and algorithms adapted for determining cardiac output, it will be recognized that the method or providing treatment described herein is more broadly applicable to treatment based on the assessment of any hemodynamic property or parameter based on e.g., multi-source analysis.

As shown in FIG. 4, the method of providing treatment 400 generally comprises first disposing a plurality of impedance cardiography electrodes (see e.g., FIGS. 2a and 2b) with respect to the thoracic cavity of the subject per step 402. As previously discussed, the electrodes 200 are the single or multi-terminal type with heart sounds capability (or other suitable configuration), and are disposed above and below the thorax of the subject such that at least one stimulation terminal and one excitation terminal are above and below the thorax. Next, the impedance waveform (and ECG and heart sounds) data of the subject are measured non-invasively via the electrodes per step 404; specifically by applying a constant AC waveform to the stimulation terminal(s), and measuring the resultant voltage at the measurement terminal(s), as well as utilizing the acoustic sensor 212 previously described for heart sounds. In step 406, the stroke volume of the subject's cardiac muscle during at least one cardiac cycle is determined using the multi-source detection and validation methodologies previously discussed herein. The stroke volume is determined from the derived hemodynamic characteristics of the waveform; such as for example in one embodiment via LVET and $dZ/dt_{max}$. The cardiac output (CO) of the subject is next determined in step 408 based on the stroke volume determined in step 406, and the heart rate (HR) derived from the subject from, for example, the ECG waveform or the heart sounds sensor.

Figure 1A:
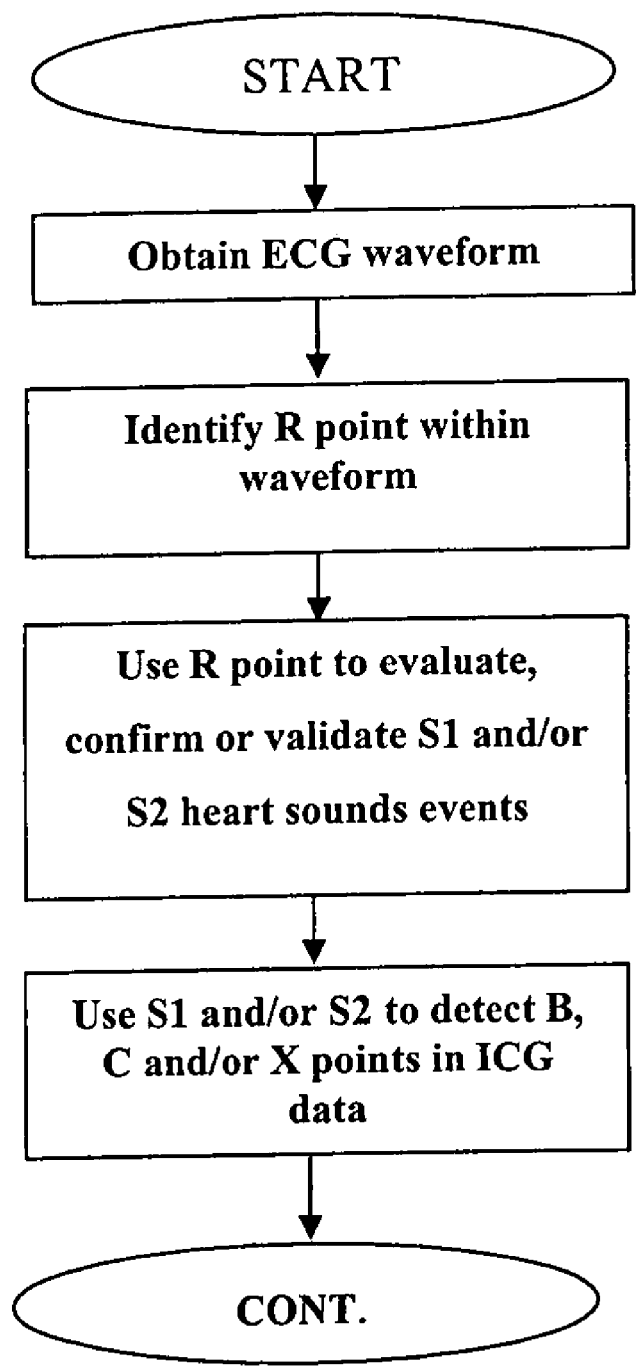
FIG. 1a is a logical flow chart illustrating one specific implementation of the generalized method of FIG. 1 in the context of heart sounds/ICG/ECG data.
Figure 1B:
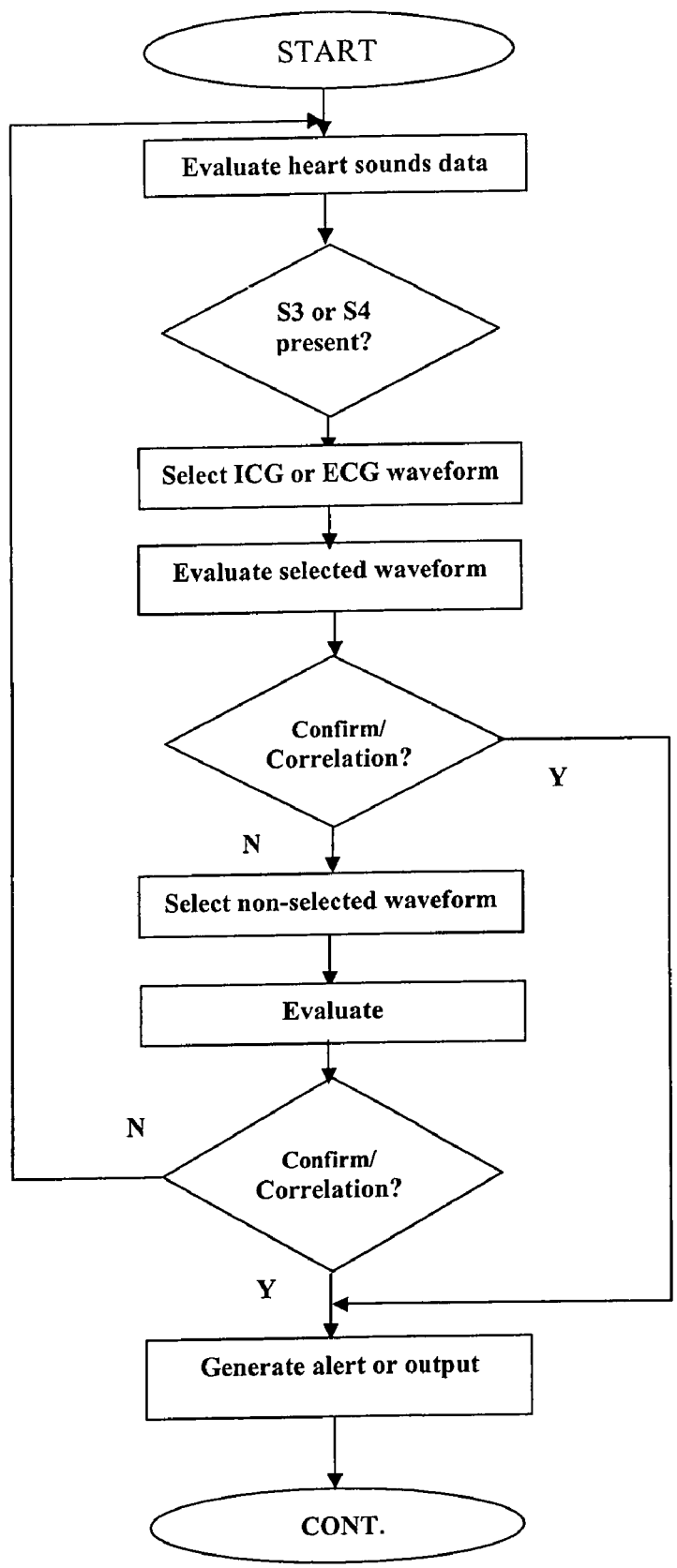
FIG. 1b is a logical flow diagram illustrating one embodiment of the method of identifying a particular condition (e.g., impending or actual heart failure) using the multi-source approach of the invention.

Per step 408, a diagnosis or assessment of the subject's condition may also be performed, such as based on the identification of one or more artifacts or shapes of interest (e.g., the presence of S3 or S4, and correlation/confirmation thereof, as shown in FIG. 1a), as previously described.

Lastly, a course of treatment is determined and provided to the subject based on the cardiac output (CO) of step 410. Such course of treatment may include, for example, the intravenous injection of pharmacological agents, angioplasty, or other such measures aimed at increasing cardiac output or otherwise stemming further degradation of the subject's cardiac function.

It will be noted that the methods of treatment described herein may be used in a "feedback" fashion; i.e., the response to one or more courses of treatment or therapy can be monitored for indications of proper (or improper) patient response, or unexpected reactions. In this fashion, the course of treatment or therapy can be confirmed. Moreover, the actual monitoring of the subject can be altered based on this feedback; for instance, if a patient being monitored is going into shock, or being anesthetized, the pulse or cardiac performance may be affected, thereby necessitating different monitoring parameters/settings, or even different strategies.

Defibrillation Apparatus and Methods

In another aspect of the invention, an improved defibrillation apparatus and methods are disclosed. Specifically, the use of a heart sounds sensor provides data regarding the shock/no-shock decision. See, e.g., U.S. Pat. No. 7,149,576 issued Dec. 12, 2006 entitled "Apparatus and Method for Defibrillation of a Living Subject", incorporated herein by reference in its entirety, which discloses defibrillation apparatus and methods which use impedance cardiography techniques for accurately determining if and when a countershock should be applied to the subject. This approach for determination of shockable and nonshockable rhythms, including for example VT (Ventricular Tachycardia) and SVT (Supra-ventricular tachycardia), determines if significant and pulsatile cardiac output (blood flow through the heart) is present with each heartbeat. In one exemplary embodiment of the apparatus, electrodes (which may also have a predetermined terminal spacing) are utilized to ensure ICG waveform features are captured with sufficiently high resolution. Pacing spike detection is implemented to prevent misclassification of pacing spikes as R points. A wavelet algorithm for efficient R point detection during arrhythmias is also used in conjunction with the foregoing. Various wavelets and scaling functions are utilized as part of the invention to emphasize certain features of interest associated with the input impedance and/or ECG waveforms obtained from electrodes positioned on the subject's thorax. The resulting emphasized feature in each wavelet transform is then detected to obtain a fiducial point (e.g., B, C, X for the impedance waveform, and R for the ECG waveform). By virtue of its transformation to the time-scale domain, this wavelet method is more resistant to noise artifact than empirical waveform processing in the time domain.

Furthermore, no absolute thresholds are used for R, B, C, or X point detection in the exemplary embodiment, which increases the ability of this algorithm to generalize among waveforms from the cardiac patient population. This capability can also be enhanced through the use of heart sounds information as previously described herein. The use of a decision model not constrained to discrete values or absolute thresholds (e.g. a fuzzy logic model) ensures that the decision module is capable of such generalization. With efficient beat detection, the variability of B point and X point samples can also advantageously be determined with higher certainty.

It will be recognized that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A computer-implemented method of assessing cardiac function within a living subject, comprising:
   obtaining:
   (i) acoustic information relating to the cardiac system of said subject, the acoustic information including a heart sound;
   (ii) electrocardiographic (ECG) information relating to said subject; and
   (iii) impedance cardiographic (ICG) information relating to said subject;
   using the ECG information to validate a timing of the heart sound of the acoustic information so as to provide a validated sound event of the acoustic information;
   using the validated sound event of the acoustic information to detect a fiducial point of the ICG information; and
   utilizing said acoustic, ECG and ICG information substantially in concert to assess cardiac function.

2. The method of claim 1, wherein said act of obtaining acoustic and ECG information are utilized to improve ICG fiducial point detection in said obtained ICG information.

3. The method of claim 2, further comprising:
   confirming the timing of cardiac sounds within said obtained acoustic information utilizing at least in part a portion of said obtained ECG information; and
   detecting one or more ICG fiducial points utilizing at least in part the confirmed timing within said obtained acoustic information.

4. The method of claim 3, wherein said cardiac sounds comprise S1 and S2 heart sounds.

5. The method of claim 4, wherein said one or more ICG fiducial points comprises a "B" point and a "X" point in said obtained ICG information.

6. The method of claim 3, wherein said portion of said ECG information comprises an "R" point reference.

7. The method of claim 1, wherein said acoustic and ECG information are utilized to improve classification of a plurality of ICG waveforms.

8. The method of claim 1, wherein said obtained ECG and ICG information are utilized to improve the characterization of said acoustic information.

9. The method of claim 1, further comprising:
disposing a sensor apparatus on the thoracic cavity of the living subject, said sensor apparatus comprising a plurality of terminals and an acoustic receptor device.

10. The method of claim 9, wherein said acts of obtaining acoustic and ECG information are utilized to improve ICG fiducial point detection.

11. The method of claim 10, further comprising:
confirming the timing of cardiac sounds within said obtained acoustic information utilizing at least in part a portion of said ECG information; and
detecting one or more ICG fiducial points in said obtained ICG information utilizing at least in part the confirmed timing within said obtained acoustic information.

12. The method of claim 9, wherein said steps of obtaining acoustic and ECG information are utilized to improve classification of a plurality of ICG waveforms.

13. The method of claim 9, wherein said steps of obtaining ECG and ICG information are utilized to improve the characterization of said obtained acoustic information.

14. The method of claim 1, further comprising: utilizing a duration of at least a portion of said acoustic information relative to a duration of a QRS complex duration obtained from said ECG information.

15. The method of claim 14, wherein said duration of at least a portion of said acoustic information comprises determining a duration of cardiac sounds from an onset point to a termination point of a particular sound.

16. The method of claim 14, further comprising identifying one or more ICG fiducial points in said obtained ICG information by utilizing, at least in part, said duration.

17. The method of claim 1, further comprising:
disposing a sensor apparatus on the thoracic cavity of the living subject; and
optimizing at least one pacemaker setting based at least in part on said assessment of cardiac function.

18. The method of claim 17, wherein said sensor apparatus comprises a plurality of electrically conductive terminals and an acoustic receptor device.

19. The method of claim 17, wherein said at least one pacemaker setting comprises a setting for AV or VV timing.

20. The method of claim 1, further comprising:
disposing a sensor apparatus on the thoracic cavity of a living subject;
beginning a course of treatment for said subject; and
utilizing subsequently obtained acoustic, ECG, and ICG information to assess cardiac function resulting from said treatment.

21. The method of claim 1, further comprising:
evaluating the heart sound so as to provide an unvalidated sound event of the acoustic information;
segregating the unvalidated sound event from the validated sound event; and
using the unvalidated sound event to detect another fiducial point of the ICG information.

22. A computer-implemented method of assessing cardiac function within a living subject, comprising:
obtaining acoustic information relating to the cardiac system of said subject, the acoustic information including a heart sound;
obtaining electrocardiographic (ECG) signals relating to said subject; and
obtaining impedance cardiographic (ICG) signals relating to said subject;
converting said acoustic information into electrical acoustic signals, and providing said acoustic, ECG, and ICG signals to a processing device;
using the ECG signals to validate a timing of the heart sound of the acoustic information so as to provide a validated sound event of the acoustic information;
using the validated sound event of the acoustic information to detect a fiducial point of the ICG signals; and
utilizing said acoustic, ECG and ICG signals to form a profile of the cardiac function of said living subject.

23. The method of claim 22, wherein said acoustic signals are provided to said processing device over a conductor, said conductor also carrying said ICG and ECG electrical signals to said processing device.

24. The method of claim 22, wherein said processing device comprises a digital processor, and said method further comprising converting said acoustic, ECG and ICG signals from an analog domain to a digital domain.

25. The method of claim 22, wherein said acoustic signals are provided to said processing device over a wireless data link.

26. The method of claim 22, wherein said acoustic signals are transported to a component remote from said living subject, and subsequently converted into electrical signals.

27. The method of claim 22, further comprising:
utilizing said obtained acoustic and ECG signals to uniquely characterize at least portions of an ICG waveform; and
separating said characterized portions into at least two different classifications.

28. The method of claim 27, wherein said separation is performed by a signal processing algorithm.

29. The method of claim 27, wherein said separation is performed manually by a user, said manual separation being accomplished via at least a graphical user interface.

30. The method of claim 22, further comprising:
evaluating the heart sound so as to provide an unvalidated sound event of the acoustic information;
segregating the unvalidated sound event from the validated sound event; and
using the unvalidated sound event to detect another fiducial point of the ICG signals.

31. A computer-implemented method of assessing cardiac regurgitation within a living subject, comprising:
obtaining acoustic information relating to the cardiac system of said subject, the acoustic information including a heart sound;
obtaining electrocardiographic (ECG) information relating to said subject; and
obtaining impedance cardiographic (ICG) information relating to said subject;
using the ECG information to validate a timing of the heart sound of the acoustic information so as to provide a validated sound event of the acoustic information;
using the validated sound event of the acoustic information to detect a fiducial point of the ICG information; and
utilizing said acoustic, ECG and ICG information collectively to assess cardiac regurgitation within said subject.

32. The method of claim 31, wherein said acts of obtaining acoustic and ECG information are utilized at least in part to determine a location within the subject's heart of said regurgitation.

33. The method of claim 31, further comprising:
evaluating the heart sound so as to provide an unvalidated sound event of the acoustic information;
segregating the unvalidated sound event from the validated sound event; and
using the unvalidated sound event to detect another fiducial point of the ICG information.

34. A computer-implemented method of assessing quality of cardiac data obtained from a living subject, comprising:
obtaining acoustic information relating to the cardiac system of said subject, the acoustic information including a heart sound;
obtaining electrocardiographic (ECG) information relating to said subject;
obtaining impedance cardiographic (ICG) information relating to said subject;
using the ECG information to validate a timing of the heart sound of the acoustic information so as to provide a validated sound event of the acoustic information;
using the validated sound event of the acoustic information to detect a fiducial point of the ICG information; and
utilizing said acoustic, ECG and ICG information to assess the quality of one or more cardiac beats.

35. The method of claim 34, further comprising:
evaluating the heart sound so as to provide an unvalidated sound event of the acoustic information;
segregating the unvalidated sound event from the validated sound event; and
using the unvalidated sound event to detect another fiducial point of the ICG information.

* * * * *